United States Patent
Hamamoto et al.

(10) Patent No.: US 6,909,173 B2
(45) Date of Patent: Jun. 21, 2005

(54) FLEXIBLE SUBSTRATE, SEMICONDUCTOR DEVICE, IMAGING DEVICE, RADIATION IMAGING DEVICE AND RADIATION IMAGING SYSTEM

(75) Inventors: Osamu Hamamoto, Kanagawa (JP); Koji Sato, Kanagawa (JP); Kenji Kajiwara, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/165,319

(22) Filed: Jun. 10, 2002

(65) Prior Publication Data

US 2002/0195676 A1 Dec. 26, 2002

(30) Foreign Application Priority Data

Jun. 13, 2001 (JP) ........................................ 2001/178844

(51) Int. Cl.[7] .......................... H01L 23/48; H01L 23/52
(52) U.S. Cl. ....................................... 257/690; 257/736
(58) Field of Search ................................ 257/690, 736, 257/390

(56) References Cited

U.S. PATENT DOCUMENTS

| | | | | |
|---|---|---|---|---|
| 3,838,984 A | * | 10/1974 | Crane et al. ................. | 428/594 |
| 4,063,993 A | | 12/1977 | Burns .......................... | 156/659 |
| 4,796,132 A | * | 1/1989 | Dekura et al. .............. | 360/126 |
| 4,810,881 A | | 3/1989 | Berger et al. ........... | 250/370.01 |
| 6,329,708 B1 | * | 12/2001 | Komiyama .................. | 257/678 |
| 2002/0021786 A1 | | 2/2002 | Hamamoto et al. ......... | 378/189 |
| 2002/0038851 A1 | | 4/2002 | Kajiwara et al. ........... | 250/368 |
| 2002/0113759 A1 | * | 8/2002 | Levine et al. .................. | 345/55 |

FOREIGN PATENT DOCUMENTS

| | | |
|---|---|---|
| FR | 2 657 694 | 8/1991 |
| JP | 2000-235629 | 8/2000 |
| JP | 2001-90278 | 4/2001 |

* cited by examiner

*Primary Examiner*—Howard Weiss
(74) *Attorney, Agent, or Firm*—Fitzpatrick, Cella, Harper & Scinto

(57) ABSTRACT

The invention concerns a flexible substrate comprising an inner lead connected to an external connection terminal formed on a substrate, and a base film formed on the lead. The base film area above the substrate and closest to the terminal is thinner than the terminal. The invention also provides a semiconductor device comprising an inner lead connected to an external connection terminal formed on a substrate, and a base film formed on the lead. The base film area above the substrate and closest to the terminal is thinner than the terminal. The invention also provides for a manufacturing method a semiconductor device comprising a substrate, an external connection terminal, and an inner lead with a base film. Further, the invention provides a semiconductor device with a substrate with a chamfered corner between the connection and side faces. By the invention, connection of an inner lead or a flexible substrate is made easier.

8 Claims, 16 Drawing Sheets

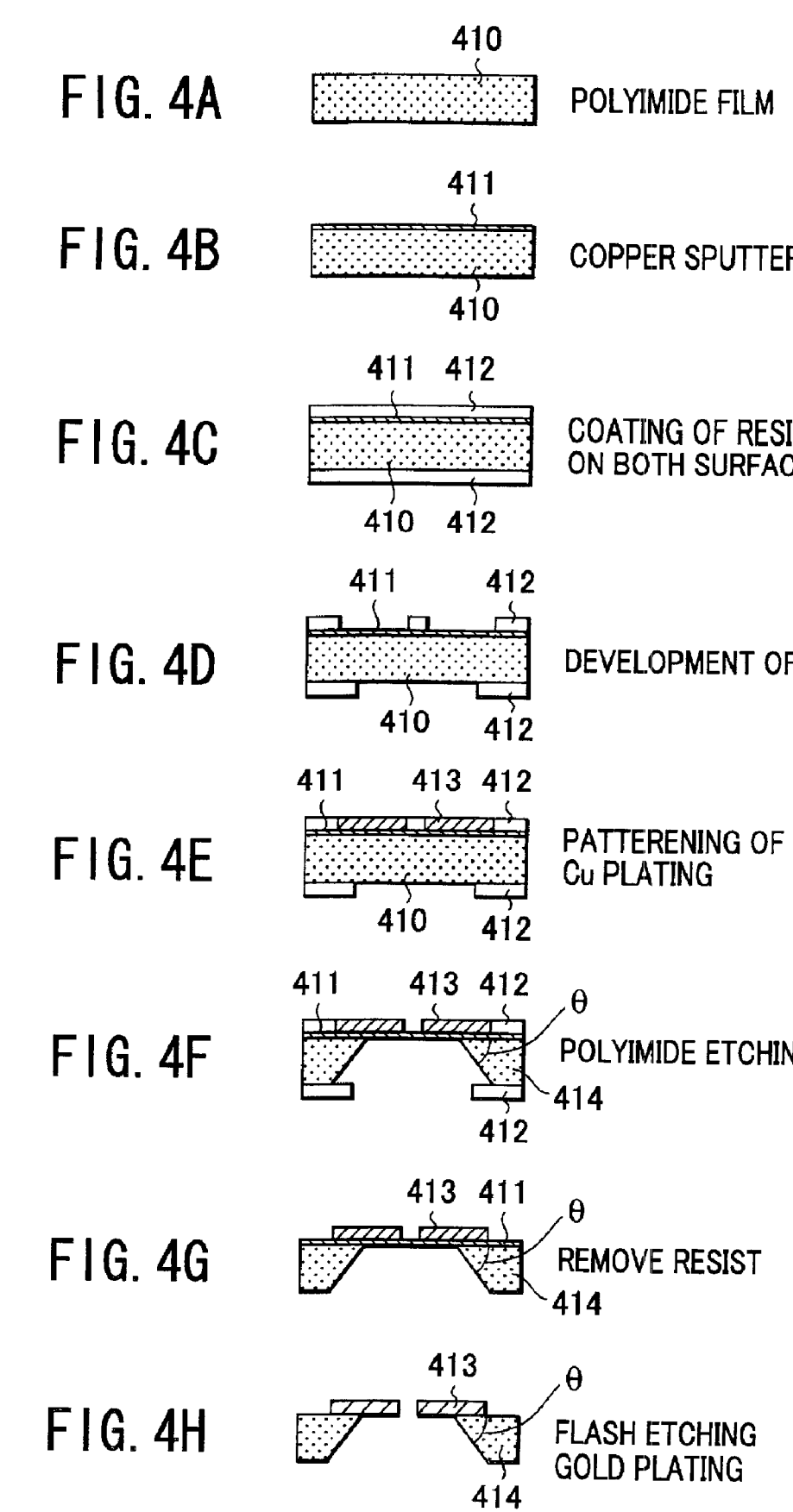

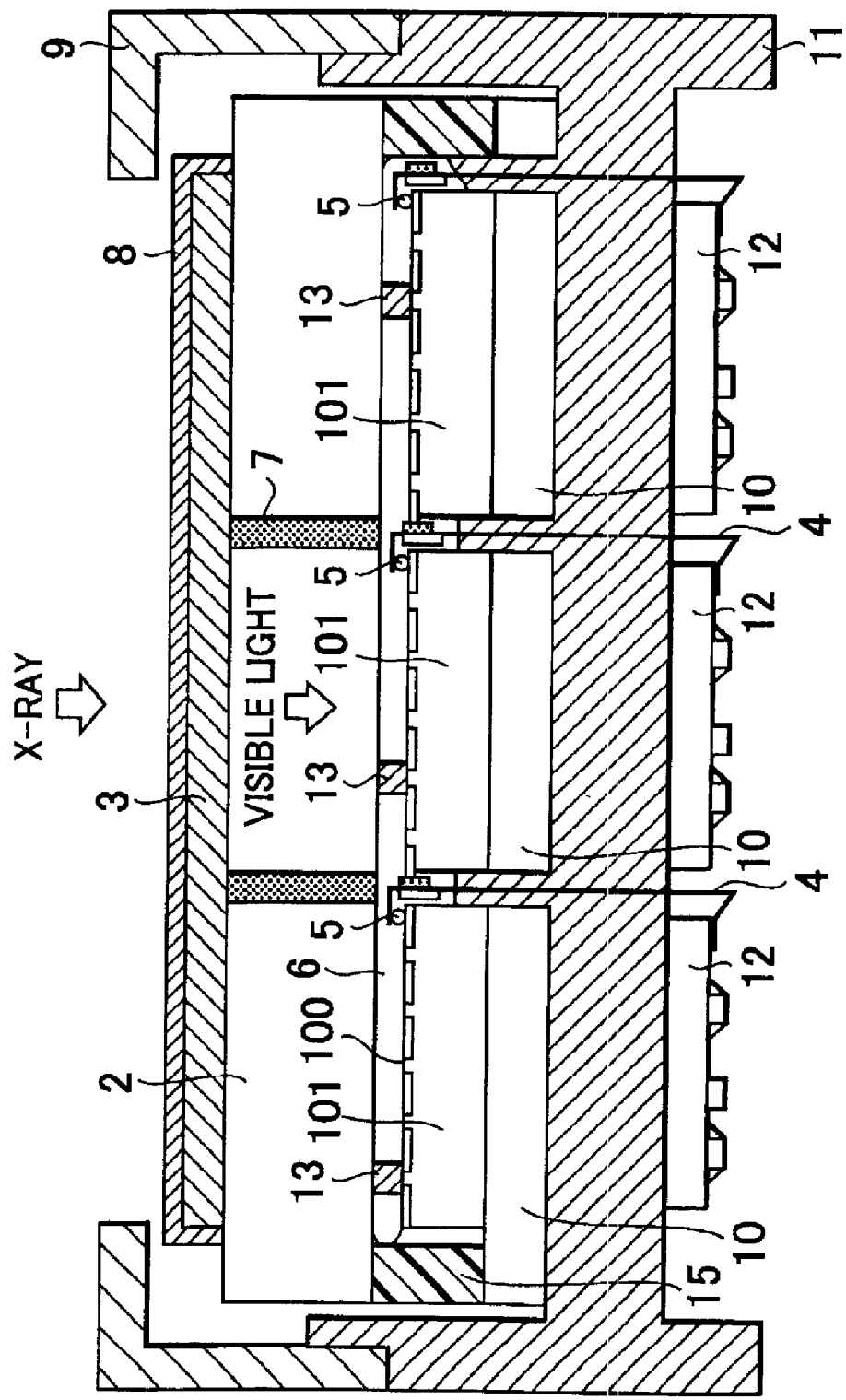

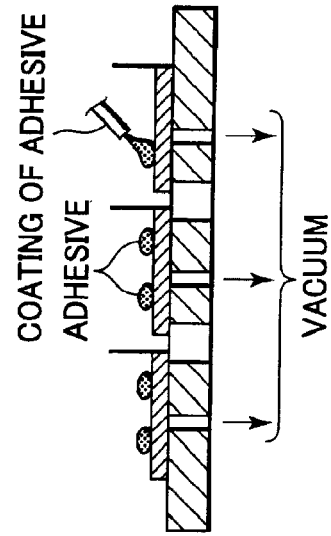
FIG. 9A
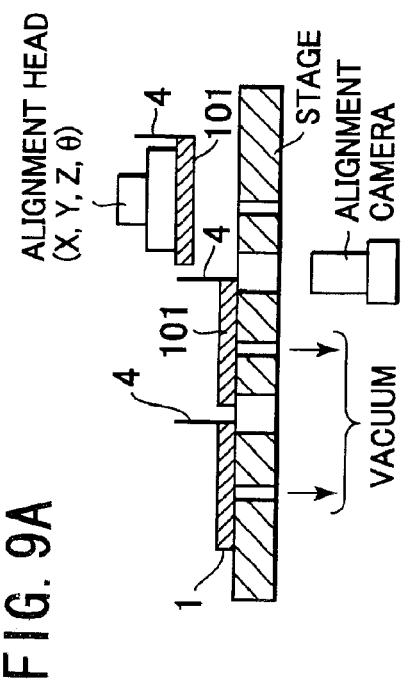
FIG. 9B
FIG. 9C
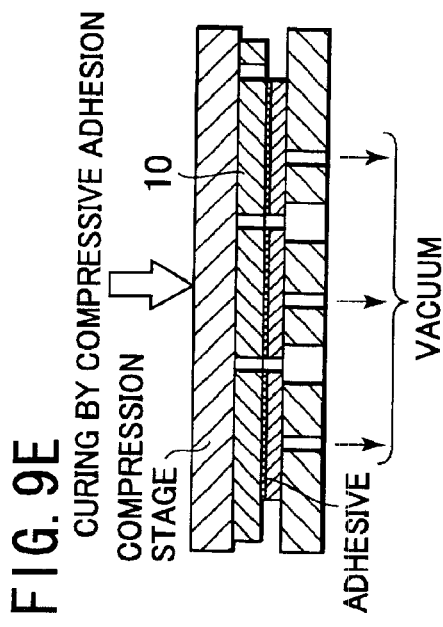
FIG. 9D
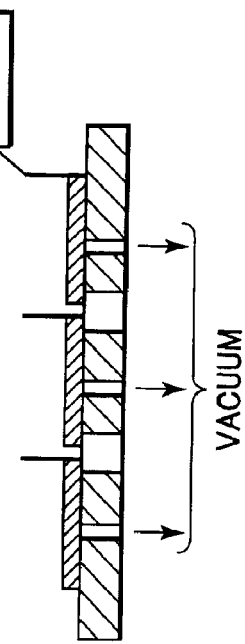
FIG. 9E
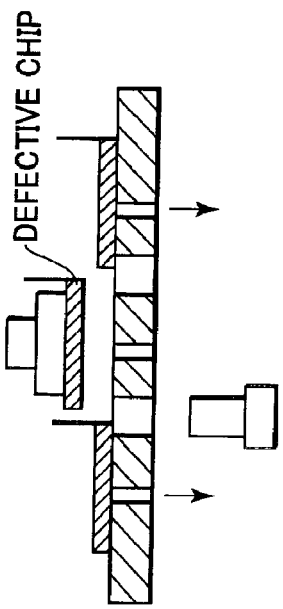
FIG. 9F

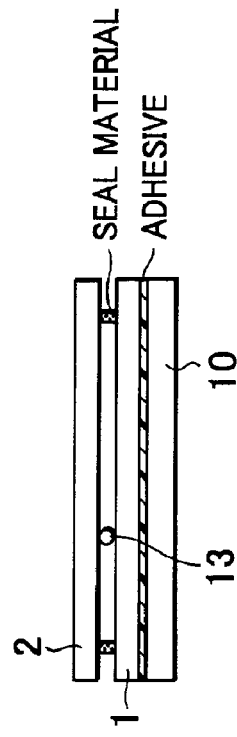
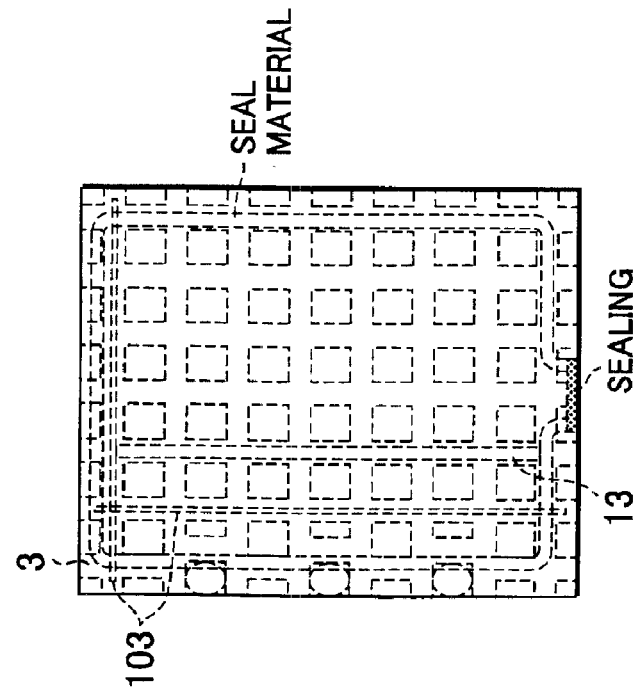
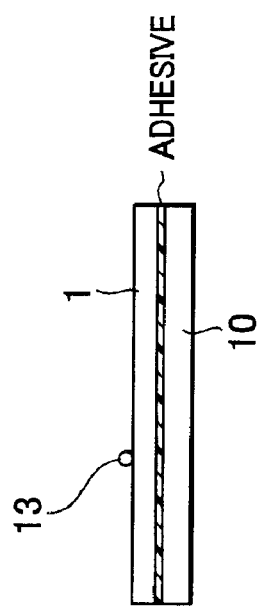
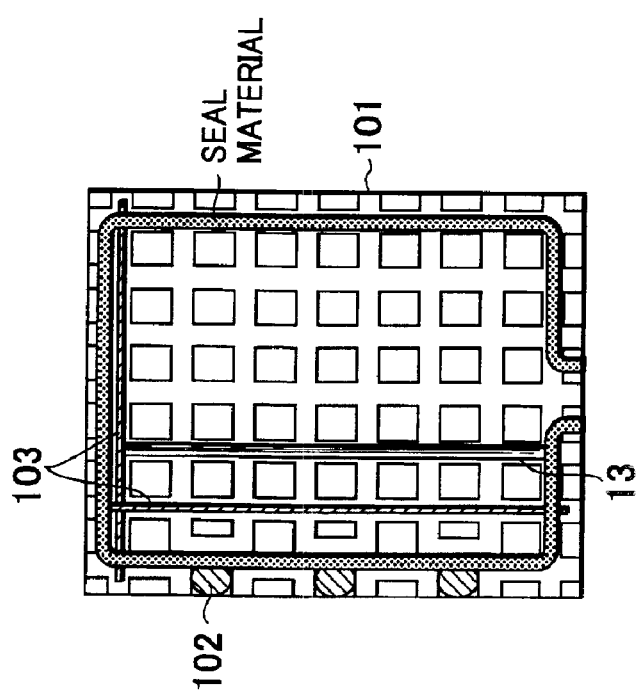

FLEXIBLE SUBSTRATE, SEMICONDUCTOR DEVICE, IMAGING DEVICE, RADIATION IMAGING DEVICE AND RADIATION IMAGING SYSTEM

BACKGROUND OF THE INVENTION

1. Field of the Invention

The present invention relates to a flexible substrate, semiconductor device, imaging device, radiation imaging device and radiation imaging system. In particular, the present invention relates to a flexible substrate, radiation imaging device and radiation imaging system for use in a medical X-ray imaging system and an industrial non-destructive inspection system.

The radiation is defined in this specification to include X-ray, α-ray, β-ray and γ-ray.

2. Related Background Art

A radiation imaging device, particularly an X-ray imaging device for medical use has been required to be able to obtain animated images, to have high image quality, to be thin and to have a large input area. An inexpensive and thin-type X-ray imaging device having a large imaging area is also required in not only a medical imaging system but also in an industrial non-destructive inspection system.

An example of such an X-ray imaging device is one made to have a large imaging area by avoiding non-light receiving parts of a CCD (Charged Coupled Device) sensor from interfering with each other by providing steps on a fiber plate.

A schematic cross section of the conventional X-ray imaging device is shown in FIG. 14. FIG. 14 shows a fluorescent layer 3 comprising a scintillator for converting X-ray into a visible light, a fiber plate 2 comprising optical fibers for guiding the visible light converted with the fluorescent layer 3 to an imaging element 1 side, and the imaging element 1 (substrate) for converting the visible light transmitted to the fiber plate 2 into an electric signal.

The fiber plate 2 is formed with an inclination to the imaging element 1 in this X-ray imaging device, in order to provide a control device (not shown), which controls reading of electric signals from each imaging element 1 by addressing each imaging element 1 between two adjoining imaging elements 1. Since no X-ray impinges on the control device, noises by the incident X-ray can be suppressed from generating by using the fiber plate 2 as described above.

FIG. 15 shows a schematic perspective view of another conventional X-ray imaging device. The same reference numerals are given in FIG. 15 to the same parts as those in FIG. 14. In the X-ray imaging device shown in FIG. 15, three imaging elements 1 are arranged as a set, for example, by changing the length of the fiber plate 2, and a step is provided for each set to provide a control device for each imaging element 1. However, since the X-ray may impinge on the control device provided at the periphery depending on the size of the fluorescent layer, a X-ray shielding member made of, for example, lead should be provided around the imaging elements at the periphery for preventing the X-ray from impinging thereon.

However, the cost increases for the X-ray device shown in FIG. 14, since machining for cutting the fiber plate 2 aslant is difficult in addition to a small number of yield per one lot. Furthermore, light transmission efficiency becomes poor in each fiber in the fiber plate 2 and sensitivity of the sensor decreases by providing a slope.

While two fiber plates 2 with 2×2 blocks are bonded in FIG. 14, an area of 100×100 mm$^2$ is a limit obtainable by using the currently available fiber plate 2. However, when 3×3 blocks of fiber plate are used by changing the slope of the fiber, the fiber plate located at the periphery has a light transmittance inferior to that of the fiber plate located at the center of the pixels in each imaging element, thereby resulting in uneven output signals from each imaging element.

In the X-ray imaging device shown in FIG. 15, on the other hand, the X-ray imaging device becomes large and heavy by providing the X-ray shielding member made of lead. In addition, since strict accuracy is required for positioning between each step and imaging element, the number of manufacturing steps increases while requiring a highly precise positioning instrument.

FIG. 16 is a schematic cross section of a conventional X-ray imaging device having a good workability in the manufacturing process that is suitable for solving the problems of large size, heavy weight and high cost without decreasing sensitivity of the X-ray imaging device.

The X-ray imaging device shown in FIG. 16 comprises a fluorescent layer (wavelength conversion device) 3 as a scintillator for converting the X-ray into a detectable wavelength light such as a visible light, fiber plates 2 comprising a plurality of optical fibers for guiding the light converted with the fluorescent layer 3 to an imaging element 1 side as well as shielding members for shielding the X-ray that remains not converted with the fluorescent layer 3, an adhesive 7 for bonding adjoining fiber plates 2 with each other, a transparent adhesive 6 for bonding the fiber plate 2 with the imaging elements 1, imaging elements 1 for converting a light into an electric signal, flexible substrates 4 for exporting the electric signal from the imaging elements 1 to the outside, a bump 5 for electrically connecting the flexible substrates to the imaging elements 1, a printed circuit board 12 as a read device to which the flexible substrate 4 is connected, a protective sheet 8 made of aluminum for protecting the fluorescent layer 3, a base substrate 10 for mounting the imaging element 1, a base case 11 for holding the base substrates 10, a case cover 9 provided on the base case 11, a spacer 13 provided between the imaging element 1 and fiber plate 2 for ensuring a give space, and a seal resin 15 for isolating the imaging element 1 from the external environment.

The problems arising in the X-ray imaging device in FIGS. 14 and 15 are solved in the X-ray imaging device having the construction described above by providing the control circuit between the pixels in each imaging element 1.

Also, the flexible substrate 4 is bent and inserted through adjoining plural imaging elements 1 for electrically connecting the printed circuit board 12 to the imaging element 1.

The X-ray imaging device shown in FIG. 16 is manufactured by bonding a set of the fiber plates, in which a plurality of fiber plates 2 are bonded with the adhesive 7, with a plurality of imaging elements 1 with the transparent adhesive 6.

Otherwise, the device may be manufactured by bonding a plurality of units of the X-ray imaging device by taking the size of the imaging element 1 or fiber plate 2 as a reference.

FIG. 18 is a schematic cross section in which the area Y in FIG. 16 is enlarged. In FIG. 18, the reference numeral 401 denotes an inner lead, the reference numeral 402 denotes a base film as a film, the reference numeral 403 denotes a cover film, and the reference numeral 105 denotes an organic insulation layer for preventing a short circuit between the end portion of the imaging element 1 and the inner lead 401 and for protecting the end portion of the imaging element 1 from being broken. The flexible substrate 4 comprises the inner lead 401, base film 402 and cover film 403.

The conventional method for connecting the bump 5 and flexible substrate 4 shown in FIG. 18 will be described using FIGS. 19A and 19B.

FIGS. 19A and 19B are schematic cross sections showing the step for connecting the bump 5 and flexible substrate 4 shown in FIG. 18.

At first, the organic insulation layer 105 is formed with a thickness of 25 μm. Then, the bump 5 is formed on the imaging element 1 by a stud bump method or plating for electrically connecting the bump 5 with the flexible substrate.

Then, the bump 5 is joined with the inner lead 401 by, for example, intermetallic bonding using an ultrasonic wave. The total thickness of the flexible substrate is adjusted to be about 50 μm.

Subsequently, a jig 19 is allowed to move toward holding tables 17 and 18, or the holding tables 17 and 18 are allowed to move toward the jig 19 while holding the imaging element 1 with the holding tables 17 and 18.

However, the base film 402 cannot be extended onto the substrate in the conventional flexible substrate 4, since the base film 402 constituting the flexible substrate 4 is formed with a thickness larger than the thickness of the bump 5 as an external connection terminal on the imaging element 1 (substrate). Accordingly, an organic insulation layer 105 should be independently provided in order to prevent the inner lead 401 from forming a short circuit when it is bent.

Positioning was also necessary for suitable positional relation between the base film 402 and bump 5 before bending the flexible substrate 4.

FIG. 20 shows a schematic cross section of the flexible substrate formed by favorably positioning the relation between the base film 402 and bump 5.

FIGS. 21A and 21B show schematic cross sections of the flexible substrate 4 when the positional relation between the base film 402 and bump 5 is not appropriate.

As shown in FIG. 21A, a short circuit is formed by making the inner lead 401 have contact with the substrate 1, or the inner lead may be broken at the edge of the substrate 1, when the inner lead 401 contacts the bump 5 at a position remote from the substrate 1 with a larger distance than a prescribed position.

As shown in FIG. 21B, when the inner lead 401 contacts the bump 5 at a position closer to the substrate 1 than the prescribed position, on the other hand, the base film 402 is pushed up causing a tensile force in the inner lead 401, and creating a possibility of breaking the inner lead 401.

In FIG. 16, a high quality and high resolution sensor may be provided with little scattering of light when the gap between the fiber plate 2 and imaging element is as narrow as possible, since the light emitted from the fiber plate 2 is a diffused light. Although it is preferable for the inner lead 401 to be made thin, a thin inner lead has the tendency to break when positioning is not proper.

SUMMARY OF THE INVENTION

The present invention, for solving the foregoing problems, provides a flexible substrate comprising an inner lead, one end of which is connected to an external connection terminal, and a base film formed on the inner lead, wherein an area of the base film closest to the external connection terminal is thinner than the external connection terminal.

The present invention also provides a semiconductor device comprising a substrate, an external connection terminal formed on a substrate, an inner lead which one end is connected to an external connection terminal, and a base film formed on the inner lead, where in an area of the base film above the substrate and closest to the external connection terminal is thinner than the external connection terminal.

The present invention further provides a method for manufacturing a semiconductor device comprising a substrate, an external connection terminal, an inner lead and a base film formed on the inner lead, comprising the steps of positioning a tip of the base film closest to the external connection terminal, bonding the base film to an edge of a side wall of the substrate with an adhesive after positioning, and connecting the inner lead to the external connection terminal by bending the inner lead after bonding.

The present invention further provides a semiconductor device comprising a substrate, an external connection face of a substrate on which an external connection terminal is formed, a side face of a substrate and a flexible substrate one end of which is connected to the external connection terminal, wherein the flexible substrate is disposed along the external connection face and side face, and a corner between the external connection face and side face is chamfered.

Further objects, features and advantages of the present invention will become apparent from the following descriptions of the preferred embodiments with reference to the attached drawings.

BRIEF DESCRIPTION OF THE DRAWINGS

FIGS. 4A to 4H are schematic cross sections showing the consecutive steps of a method for forming the flexible substrate in the third embodiment according to the present invention.

FIG. 8 is a schematic cross section of the radiation imaging device in the sixth embodiment, mounting the flexible substrate according to the present invention shown in the first, second and third embodiments.

FIGS. 9A to 9F are schematic cross sections showing consecutive steps for bonding the substrate on which the flexible substrate according to the present invention is mounted with the base substrate in the method for manufacturing the radiation imaging device in the sixth embodiment.

FIGS. 11A to 11D are drawings showing consecutive steps for bonding the photoelectric conversion substrate on which the flexible substrate according to the present invention with the fiber plate in the method for manufacturing the radiation imaging device in the sixth embodiment.

DESCRIPTION OF THE PREFERRED EMBODIMENTS

The embodiments of the present invention will be described with reference to the attached drawings.
First Embodiment FIG. 1 is a schematic cross section of the semiconductor device with a flexible substrate in the first embodiment according to the present invention.

Figure 1:
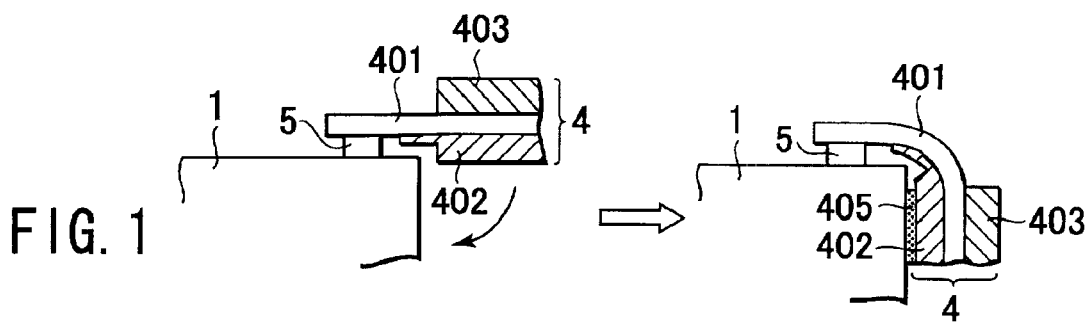
FIG. 1 is a schematic cross section of the semiconductor device with a flexible substrate in the first embodiment according to the present invention.

In FIG. 1, the reference numeral 1 denotes a substrate, the reference numeral 4 denotes a flexible substrate comprising an inner lead 401, a base film 402 as a film and a cover film 403.

One end of the flexible substrate 4 shown in FIG. 1 is connected to a bump 5 formed on the substrate 1, and the film region disposed on the substrate 1 of a base film 402 is thinner than the bump 5.

A practical method for forming the tip of the base film 402 in which the substrate 1 side is tapered with a gradation toward the substrate 1 will be described hereinafter. In a first step, a thin film of copper is deposited on a polyimide film as the base film 402 by sputtering. Then, a photo-resist is coated on both surfaces of the polyimide film to obtain a desired pattern by exposing to a light, thereby forming an electrical wiring pattern and a polyimide film pattern on a copper foil surface and on a surface having no copper foil, respectively. Then, copper is selectively plated on the required pattern. Subsequently, holes are perforated on the polyimide film by etching, where etching is suspended at a half-etching stage. The photo-resist is coated on the etched region that is desired to remain as a step, followed by obtaining a desired pattern by exposing to a light. A base film 402 with a gradation of the steps is obtained by repeating the coating and etching steps. The resist is finally removed and, after separating patterns by flash etching of copper, a flexible substrate is obtained by plating gold.

Figure 18:
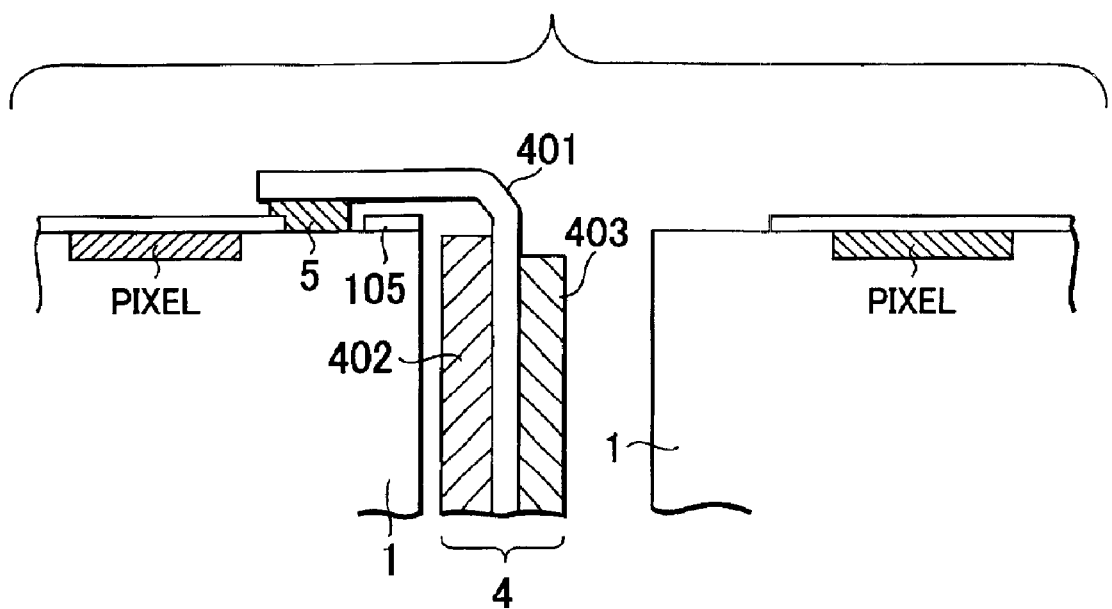
FIG. 18 is a schematic cross section in which the area Y in FIG. 16 is enlarged.
Figure 19A:
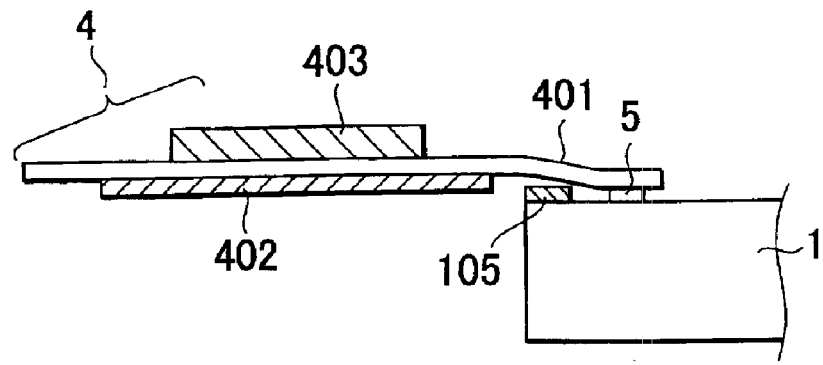
FIG. 19A is a schematic cross section showing a step for connecting the bump with the flexible substrate shown in FIG. 18.
Figure 19B:
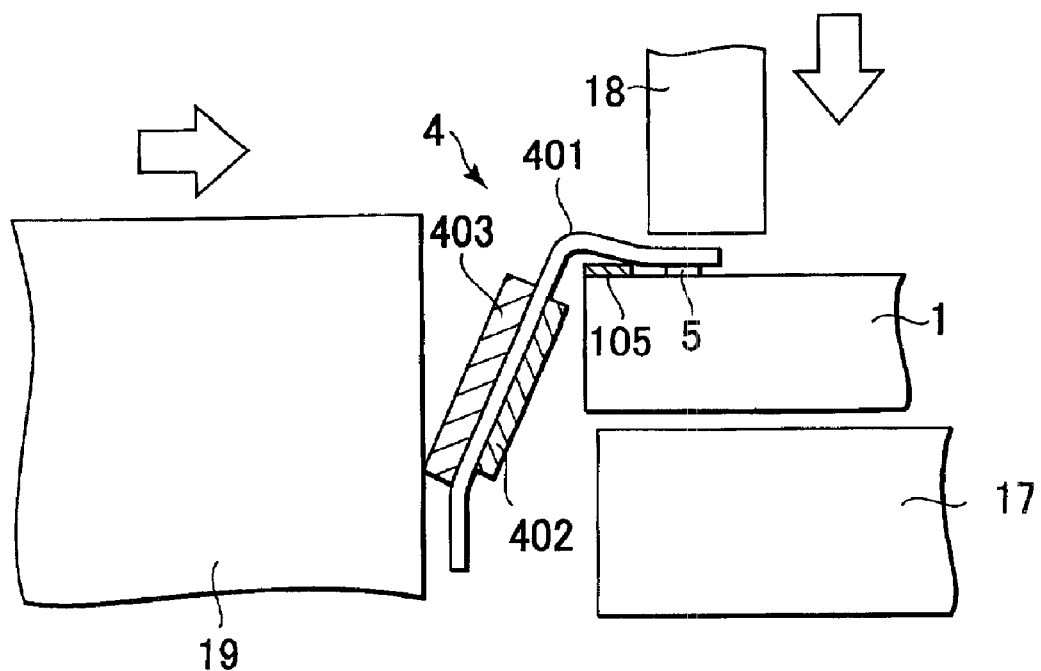
FIG. 19B is a schematic cross section showing another step for connecting the bump with the flexible substrate shown in FIG. 18.
Figure 20:
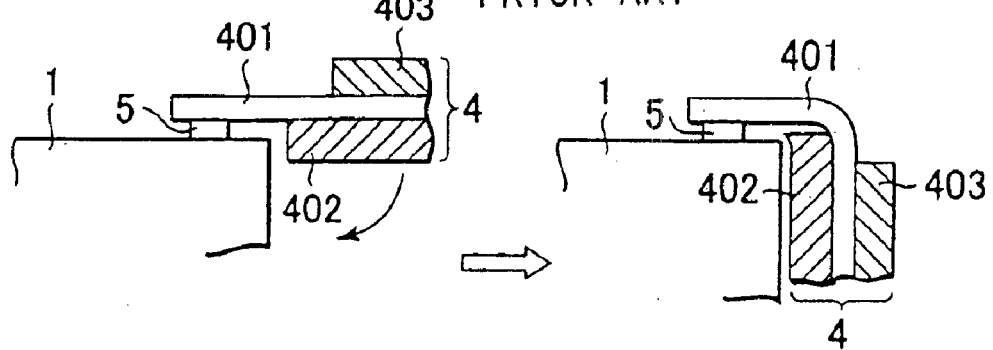
FIG. 20 is a schematic cross section of a flexible substrate in which the base film and bump are positioned with a good positional relation with each other.
Figure 21A:
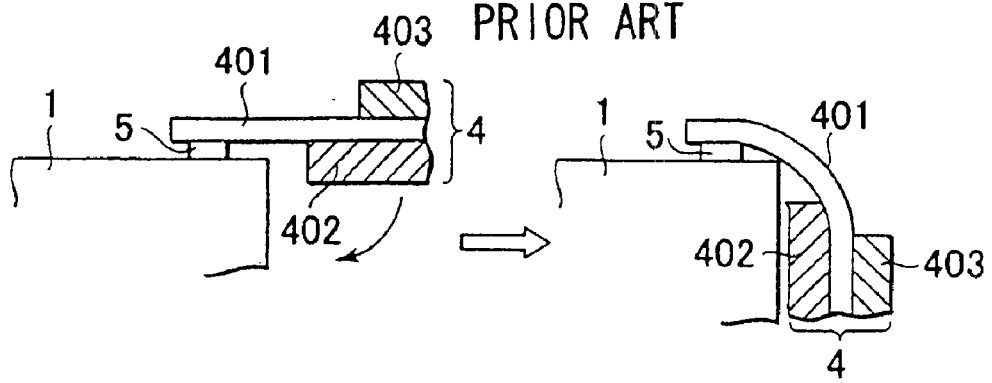
FIG. 21A is a schematic cross section of a flexible substrate in which the base film and bump are positioned with an inappropriate positional relation with each other.
Figure 21B:
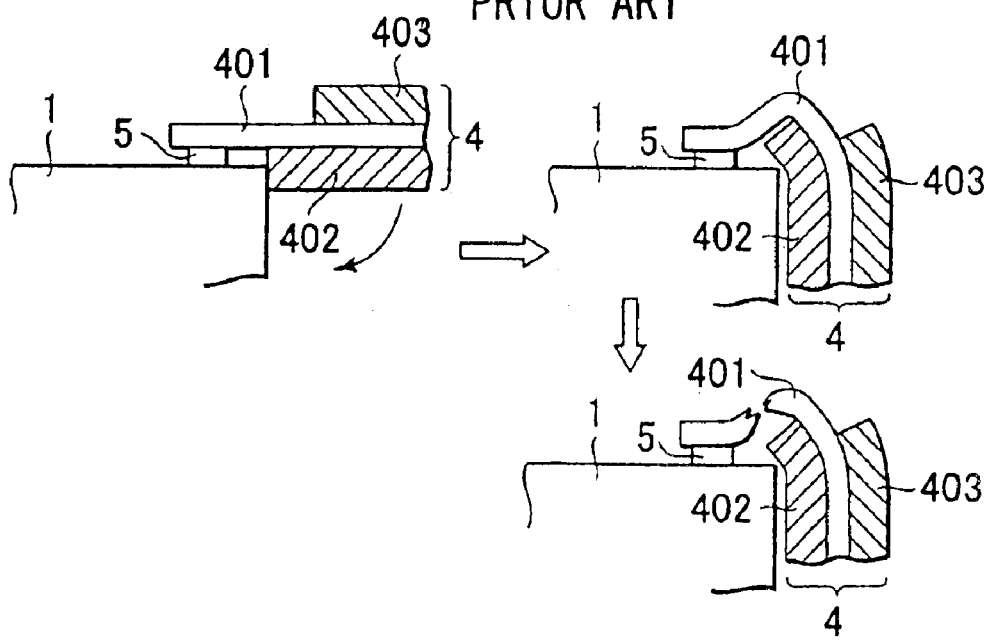
FIG. 21B is another schematic cross section of a flexible substrate in which the base film and bump are positioned with an inappropriate positional relation with each other.

It was made possible to dispose the base film 402 on the substrate as shown in this embodiment by thinning the film region to be placed on the substrate 1. Accordingly, the organic insulation layer 105 shown in FIG. 18 is not needed to enable manufacturing steps to be reduced.

Since the base film 402 is thinner than the bump 5, the inner lead 401 is not pushed up by bending the base film 402 at the edge of the substrate 1, thereby suffering no tensile force which may cause the inner lead 401 to break.

The base film 402 is formed by using, for example, polyimide as a material. The cover film 403 is formed by using, for example, polyurethane or polyimide as a material. However, these materials are not restricted thereto, and any material may be used provided it is flexible.

The substrate 1 to be described in the specification may be a photoelectric conversion substrate that converts a light into a signal charge. The substrate comprises a vertical shift resistor or a horizontal shift resistor (not shown), and the substrate may be a silicone substrate or an amorphous silicon substrate. The surface of the substrate comprises a plurality of pixels arranged in a two-dimensional array, an interlayer insulation layer thereon made of a silicon oxide film, a metal wiring line made of aluminum, and a protective layer made of nitride film and/or polyimide film. The pixel is composed of a photo-diode and MOS transistor.

The flexible substrate according to the present invention may be connected to the bump 5 formed on the substrate, or may be connected to the substrate after forming the bump 5 on the flexible substrate.
Second Embodiment FIG. 2 shows a schematic cross section of the semiconductor device with a flexible substrate in the second embodiment of the present invention.

Figure 2:
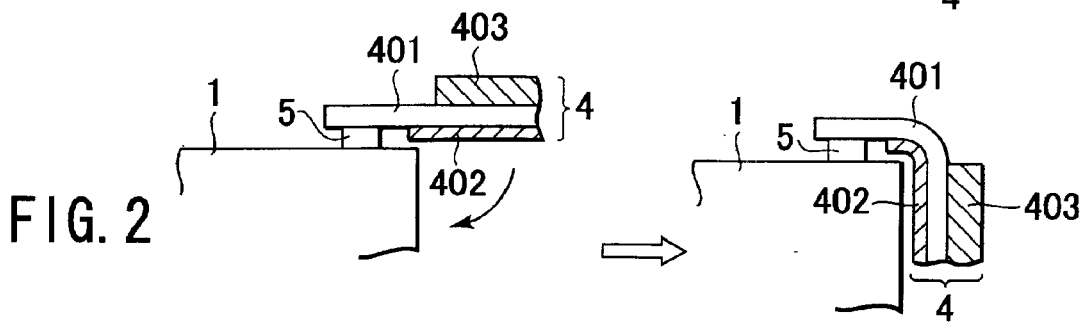
FIG. 2 is a schematic cross section of the semiconductor device with a flexible substrate in the second embodiment according to the present invention.

The substrate 4 shown in FIG. 2 is different from that in the first example in that, not only the film region of the base film 402 to be disposed on the substrate is made to be thinner than the bump 5, the entire base film 402 is made to be thinner than the bump 5. Descriptions of the reference numerals that have been already described are omitted herein.

In particular, an inner lead 401 with a thickness of about 18 μm is formed on the base film 402 with a thickness of about 12 μm. The cover film is formed by printing with a thickness of about 10 μm. Since the inner lead 401 is formed by plating, no adhesive layer is used between the base film 402 and inner lead 401 to enable the flexible substrate to be thinner. It has been difficult to reduce the thickness of the base film or inner lead when the plating method is not used.

It was made possible to dispose the base film 402 on the substrate 1 as described above by using the flexible substrate 1 in this embodiment. Accordingly, the organic insulation layer 105 as shown in FIG. 18 is not needed to enable the number of manufacturing steps to be reduced.

Since the base film 402 is thinner than the bump 5, the inner lead 401 is not pushed up by bending the base film 402 at the edge of the substrate 1, thereby preventing the inner lead 401 from breaking since no tensile force is applied.

Thinning the entire base film 402 permits, for example, the distance between the adjoining two substrates (imaging elements 1) of the plural substrates, or the distance between adjoining substrates or imaging devices when the flexible substrate 4 is disposed between the imaging devices, to be narrowed. Accordingly, it is favorable for providing a high quality and high resolution imaging device or radiation imaging device.

The flexible substrate according to the present invention may be connected to the bump 5 formed on the substrate, or may be connected to the substrate after forming the bump 5 on the flexible substrate.

Third Embodiment

Figure 3:
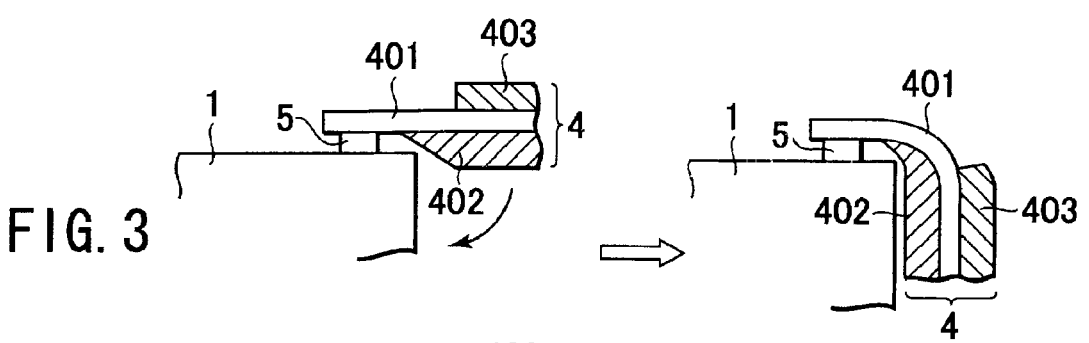
FIG. 3 is a schematic cross section of the semiconductor device with a flexible substrate in the third embodiment according to the present invention.

FIG. 3 is a schematic cross section showing the semiconductor device with a flexible substrate in the third embodiment of the present invention.

FIGS. 4A to 4H are schematic cross sections showing the method for forming the flexible substrate in the third embodiment of the present invention.

In FIGS. 4A to 4H, the reference numeral 410 denotes a polyimide film that serves as a base film 402, the reference numeral 411 denotes a copper thin film, the reference numeral 412 denotes a photo-resist, the reference numeral 413 denotes a patterned copper plating, the reference numeral 414 denotes a patterned polyimide film, and θ denotes a taper angle. The reference numerals that have been already described will be omitted herein.

The flexible substrate 4 shown in FIG. 3 is different from those in the first and second embodiments in that the tip of the base film 402 at the substrate side has an inclined shape.

The inclined shape refers to, for example, a tapered shape in which the tip of the base film 402 at the substrate 1 side is formed to be thinner toward the substrate 1 side as shown, for example, in FIG. 3.

Consequently, it was made possible in this embodiment to dispose the film region of the base film 403 being thinner than the bump 5 on the substrate 1 as in the first and second embodiments. Therefore, the organic insulation layer as shown in FIG. 18 is not needed to enable the number of manufacturing steps to be reduced.

In addition, since the base film 402 is thinner than the bump 5, the inner lead 401 is not pushed up by bending the base film 402 at the edge of the substrate 1, thereby suffering no tensile force which may cause breakage of the inner lead 401.

A method for manufacturing the tapered flexible substrate will be described hereinafter as an example of the method for forming a flexible substrate 4 having an inclined shape.

At first, a thin film 411 of copper is deposited by sputtering (FIG. 4B) on a polyimide film 410 (FIG. 4A) that serves as the base film 402.

Then, a photo-resist 412 is coated on both surfaces of the polyimide film 410 via the thin film 411 of copper (FIG. 4C), and a desired pattern is obtained by exposing to a light (FIG. 4D). An electric wiring pattern 413 and polyimide pattern 414 are formed on the faces with the thin film of copper and without the thin film of copper, respectively (FIGS. 4E and 4F).

Holes are formed on the polyimide film 410 by etching while forming a tapered cross section of the polyimide film 410 by side etching (FIG. 4F). The photo-resist 412 and patterned polyimide film 414 are eliminated (FIG. 4G) and, after electrically separating the patterns by flush etching of copper, the flexible substrate is completed by applying gold plating (FIG. 4H).

The method for forming the flexible substrate 4 as described above permits patterning of the polyimide film 410 even when it is thin as compared with the method for forming the holes on the polyimide film 410 before patterning, since patterning of the wiring lines is initially applied.

Since holes are perforated by etching, the cross section thereof may be tapered in addition to enabling patterning accuracy between the hole and wiring pattern to be attained.

In determining the taper angle θ, a longer region of the base film 402 having an inclined shape in the direction of thickness of the bump 5 is favorable for extending an alignment margin between the edge of the substrate 1 and the inclined base film 402. The taper angle θ is about 18° in this embodiment. Since the length of the region having an inclined shape in the direction of thickness of the bump 5 is about 60 μm, the alignment margin is ±30 μm, which is enough for positioning without using any special device.

The taper angle θ is controlled, for example, by the invasion speed of the etching solution into the interface between the polyimide film 410 and patterned polyimide film 414 as a photo-resist. However, the method for controlling the taper angle θ is not restricted thereto.

For example, the taper angle θ may be controlled by changing the degree of invasion of the etching solution into the interface by controlling tightness of adhesion between the polyimide film 410 and photo-resist. In one example, the amount of an adhesion enhancing agent to be blended in the photo-resist is changed, or the baking temperature of the photo-resist is changed. Since the adhesive force is reduced by lowering the baking temperature, the taper angle θ is reduced.

The method for forming the flexible substrate in this embodiment with no use of adhesives is suitable for making the flexible substrate thin and soft as compared with the conventional flexible substrate manufactured by bonding a thin film of copper to a perforated polyimide film with an adhesive.

The flexible substrate according to the present invention may be connected to the bump 5 formed on the substrate, or may be connected to the substrate after forming the bump 5 on the flexible substrate.

Fourth Embodiment

Figure 5:
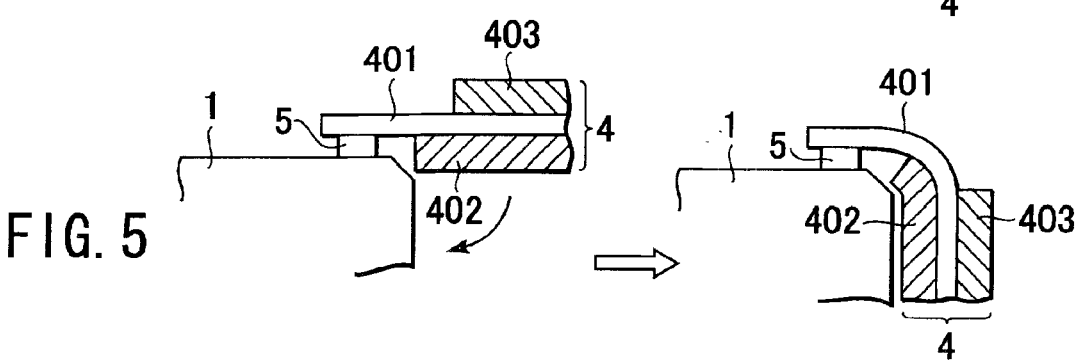
FIG. 5 is a schematic cross section of the semiconductor device with a flexible substrate in the fourth embodiment according to the present invention.

FIG. 5 is a schematic cross section of the substrate in the fourth embodiment of the present invention.

The semiconductor device is different from those in other embodiments in that the corner between the external connection face and side face of the substrate 1 is chamfered. Descriptions of the reference numerals that have been already described are omitted herein.

The external connection face as used herein refers to a face on which a bump 5 as the external connection terminal is formed.

Chamfering, as described above, allows no tensile force to be generated, since the inner lead 401 is not pushed up even when the flexible substrate 4 is disposed along the side face of the substrate 1 by bending the base film 402 at the edge of the substrate 1. Thus, the semiconductor device will seldom have a broken inner lead 401.

Figure 16:
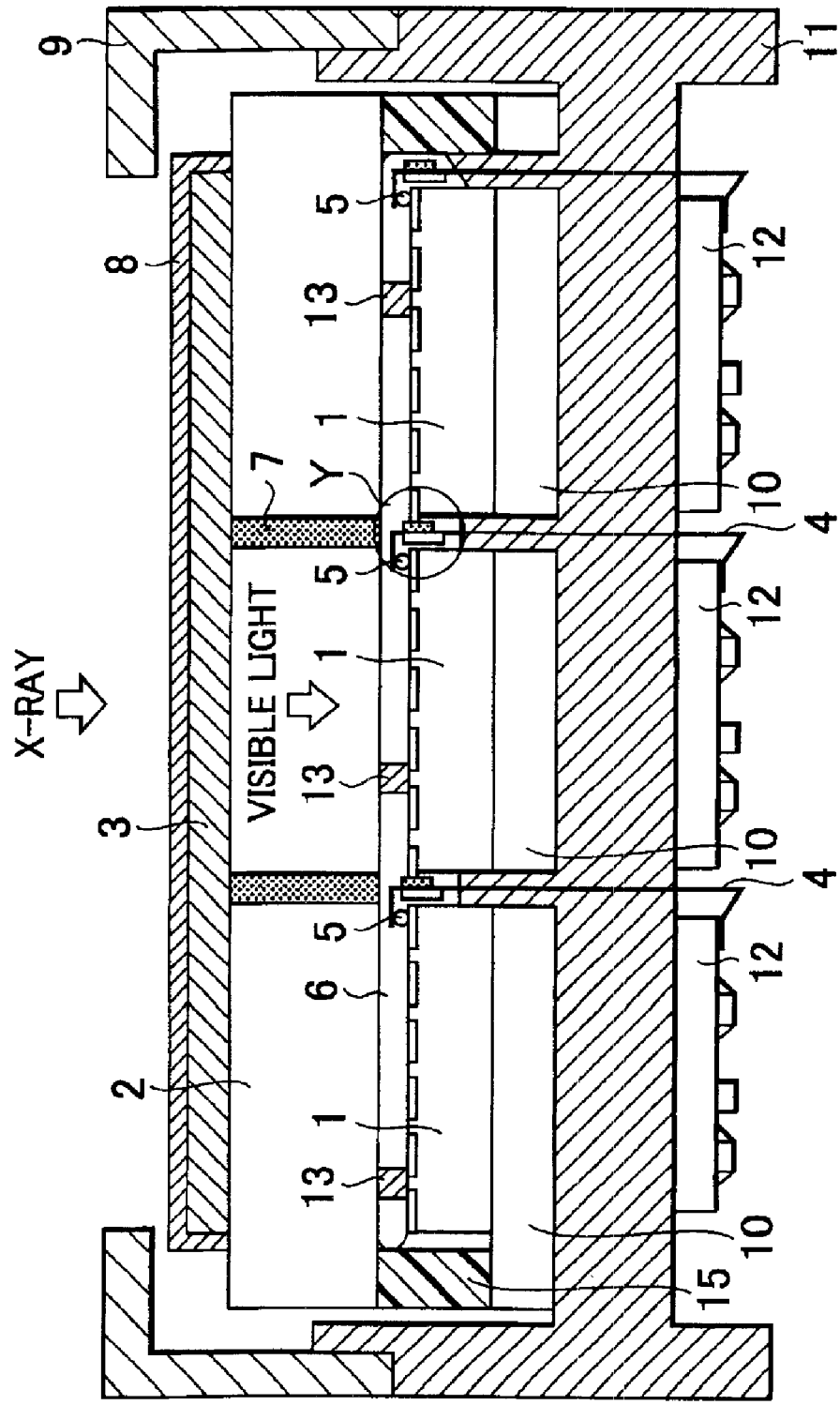
FIG. 16 is a schematic cross section of a X-ray imaging device in a conventional art for solving the problems in the X-ray imaging device in FIGS. 14 and 15.
Figure 17:
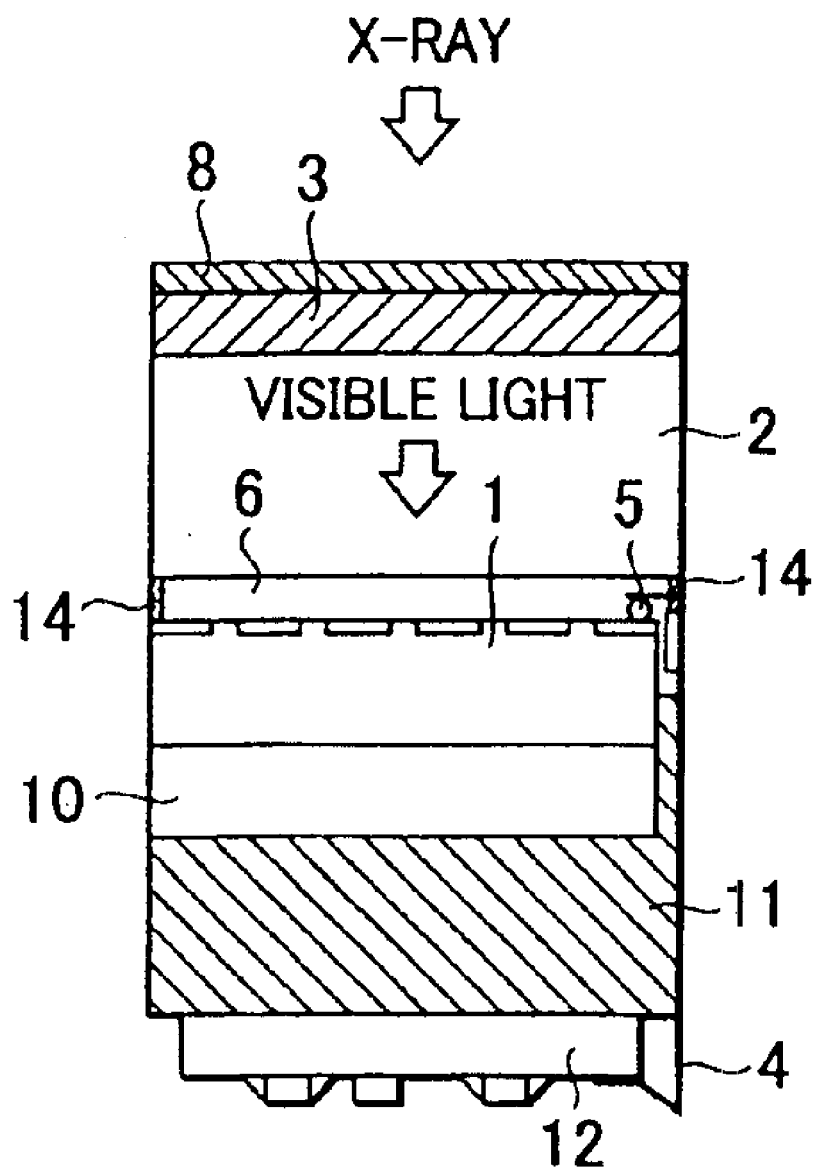
FIG. 17 is a schematic cross section of a unit of the X-ray imaging device by taking the size of the imaging element or fiber plate as a reference.

The base film 402 of the flexible substrate 4 may be thicker than the bump 5 in this embodiment. However, the distance between the two adjoining substrates (imaging elements 1) of the plural substrates, or the distance between the adjoining substrates or imaging devices when the flexible substrates are disposed between the imaging devices can be narrowed as shown, for example, in FIG. 16, by making the entire base film 402 thinner than the bump 5. Consequently, this configuration is favorable for providing a high quality and high resolution imaging device or radiation imaging device.

Fifth Embodiment

Figure 6:
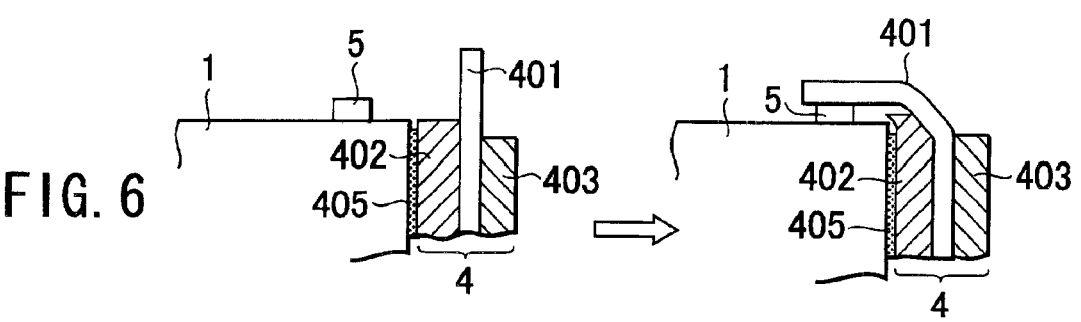
FIG. 6 is a schematic cross section showing the method for manufacturing a semiconductor device in the fifth embodiment according to the present invention.

FIG. 6 is a schematic cross section showing a method for manufacturing the semiconductor device in the fifth embodiment of the present invention.

Figure 7:
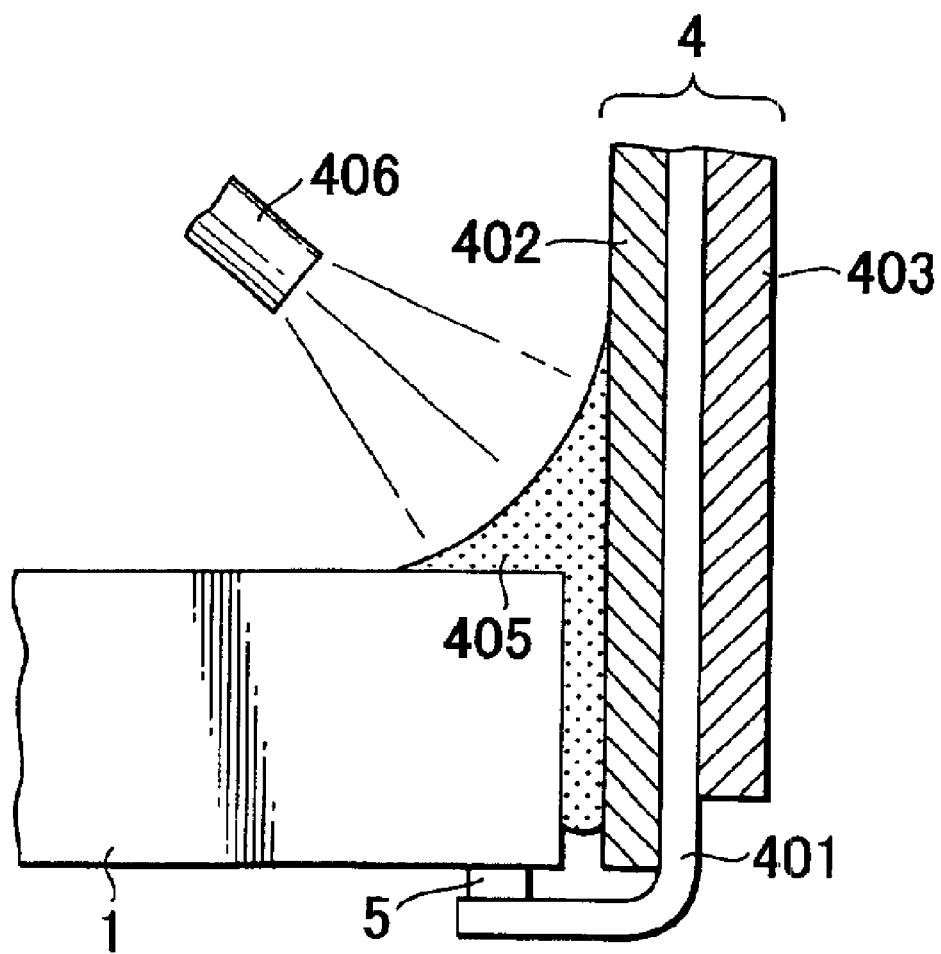
FIG. 7 is a schematic cross section showing the method for bonding the flexible substrate with the side face of the substrate.

FIG. 7 is a schematic cross section showing the step for bonding a bent flexible substrate to the side face of the substrate.

The reference numeral 405 in FIG. 6 denotes a heat and UV light curable resin as an adhesive.

The reference numeral 406 in FIG. 7 denotes a UV source. The reference numerals that has been already described are omitted herein.

FIG. 6 shows the method for connecting the inner lead 401 to the bump 5 by bending the inner lead after connecting the base film 402 to the side face of the imaging element 1 with an adhesive 405, while the tip of the base film 402 at the bump 5 side is positioned with the light incidence side of the substrate 1.

In an example, the present invention provides a method for manufacturing the semiconductor device comprising a flexible substrate 4 having a substrate 1, a bump 5, an inner lead 401 and a base film 402 covering the inner lead, comprising the steps of positioning the tip of the base film 402 at the side closer to the bump 5 with the substrate 1, bonding the base film 402 to the side face edge of the substrate 1 using an adhesive 405 while positioning them, and connecting the bent inner lead 401 to the bump 5 after bonding.

The organic insulation layer 105 shown in FIG. 18 is not needed in the configuration above, since no short circuit is formed between the inner lead 401 and substrate 1 by previously positioning the base film 402. Furthermore, the inner lead 401 is not easily broken.

The step for bonding the substrate 1 to the base film 402 will be described below with reference to FIG. 7. A UV and heat curable resin 405 is coated in the gap between the flexible substrate 4 and substrate 1 from the back-face side of the substrate 1. Then, the flexible substrate 4 is bonded to the side face of the substrate 1 by irradiating the UV and heat curable resin 405 with a UV light from a UV light source 406 while heating the resin.

When the adhesive is a resin that is cured only by the UV light that can hardly penetrate in the gap between the flexible substrate 4 and substrate 1, the non-cured adhesive may adversely affect the substrate 1 or a long time is needed for curing the adhesive in the gap. Therefore, it is desirable to use the adhesive that requires both heat and UV light for curing.

Using an adhesive sheet having a predetermined thickness as the adhesive is favorable for bonding between a plurality of substrates.

Sixth Embodiment

FIG. 8 is a cross section of the radiation imaging device as the sixth embodiment mounting the flexible substrate according to the present invention shown in the embodiments 1, 2 and 3.

In FIG. 8, the reference numeral 3 denotes a fluorescent layer (wavelength conversion device) as a scintillator for converting a radiation such as X-ray into a light such as a visible light having a detectable wavelength, the reference numeral 101 denotes a photoelectric conversion substrate having an imaging element 100 for converting a light into an electrical signal, the reference numeral 2 denotes a fiber plate comprising a plurality of optical fibers for guiding the light converted with the fluorescent layer 3 to the imaging element 100 side as well as a shielding layer for shielding the X-ray that remains not converted with the fluorescent layer 3, the reference numeral 7 denotes an adhesive for bonding adjoining two fiber plates 2 with each other, the reference numeral 6 denotes a transparent adhesive for bonding the fiber plate 2 with the photoelectric conversion substrate 101, and the reference numeral 4 denotes a flexible substrate for exporting the electric signal from the imaging element 100 to the outside, which is electrically connected to a printed circuit board 12 by being disposed among a plurality of photoelectric conversion substrates 101. The reference numeral 5 denotes a bump as an external connection terminal for electrically connecting the flexible substrate 4 with the imaging element 100, the reference numeral 12 is a printed circuit board as a read-out device to which the flexible substrate 4 is connected, the reference numeral 8 denotes a protective sheet comprising aluminum for protecting the fluorescent layer 3, the reference numeral 10 denotes a base substrate for mounting the photoelectric conversion substrate 101, the reference numeral 11 denotes a base case for holding the base substrate 10, the reference numeral 9 denotes a case cover placed on the base case 11, the reference numeral 13 denotes a spacer provided between the photoelectric conversion substrate 101 and fiber plate 2 for securing a given space, and the reference numeral 15 denotes a seal resin for isolating the photoelectric conversion substrate 101 from an outer environment.

Descriptions of the reference numerals that have been already described are omitted herein.

The photoelectric conversion substrate 101 as used in this specification denotes a substrate having an imaging element 100 for converting a light into a signal charge. Accordingly, the substrate comprises a vertical resistor and horizontal resistor (not shown), and a silicon substrate or an amorphous silicon substrate is used for the substrate. The surface of the substrate comprises a plurality of pixels arranged in a two-dimensional array, an interlayer insulation layer thereon using a silicon oxide film, a metal wiring line using aluminum, and a protective layer using a nitride or polyimide film. The pixel comprises a photodiode or MOS transistor.

While this embodiment describes a radiation imaging device, it may be an imaging device having no fluorescent layer 3 and/or a fiber plate 2.

While this embodiment shows a radiation imaging device manufactured by bonding a plurality of photoelectric conversion substrate 101, it may be a radiation imaging device comprising only one photoelectric conversion substrates 101. A radiation imaging device having a small cross sectional area relative to the light incidence area may be manufactured by bending the flexible substrate.

Otherwise, the imaging device may comprise one photoelectric conversion substrate 101 without the fluorescent layer 3 and/or the fluorescent layer 3 and fiber plate 2. The imaging device having a small cross sectional area relative to the light incidence area may be also manufactured by bending the flexible substrate.

The operation of the radiation imaging device as the X-ray imaging device will be described hereinafter with reference to FIG. 8. A X-ray source (not shown) is provided at the fluorescent layer 3 side, and a X-ray is irradiated from the X-ray source while disposing an imaging object between the X-ray source and X-ray imaging device to expose the X-ray to the imaging object. Then, the X-ray containing a line of X-ray information with a difference of intensity by permeating through the imaging object is transmitted to the X-ray imaging device side.

Almost all the X-ray arriving at the X-ray imaging device is converted into a light such as a visible light at the fluorescent layer 3 side depending on the intensity of the X-ray. The light acquired by conversion is transmitted to the photoelectric conversion substrate 101 through the fiber plate 2. Since the fiber plate 2 is bonded to the photoelectric conversion substrate 101 with a transparent adhesive 6, the light is impinged onto the imaging element 100 without any decay by passing through the transparent adhesive 6.

The X-ray remaining not converted with the fluorescent layer 3, or the X-ray not impinging on the fluorescent layer 3 advances toward the imaging element 100 side without being converted into an wavelength detectable by the imaging element 100. Such X-ray is shielded by the shielding layer incorporated in the fiber plate 2, and does not impinge on the imaging element 100 and printed circuit board 12.

The light also impinges on the adhesive layer 7. The light impinging on the adhesive layer 7 is absorbed or reflected with a small transmittance. While this light impinging on the imaging element 100 causes line defects, the pixel of the imaging element 100 is little influenced by the light from the adhesive layer 7 by forming the fiber plate 2 and photoelectric conversion substrate 101 to have the same size and by properly positioning them.

The incident light is converted into an electrical signal depending on the intensity of the light in the imaging element 100. This electrical signal is exported to the flexible substrate 4 in response to instructions from a read-out circuit (not shown). The electrical signal exported to the flexible substrate 4 is transmitted to an external circuit board (not shown) for image processing after an A/D conversion of the signal.

The manufacturing process of the radiation imaging device according to the present invention will be described hereinafter with reference to FIGS. 9A to 9C, FIGS. 10A to 10D and FIGS. 11A to 11D.

FIGS. 9A to 9F are schematic cross sections showing the steps for bonding the photoelectric conversion substrate 101 on which the flexible substrate according to the present invention is mounted with the base substrate in the manufacturing process of the radiation imaging device according to the sixth embodiment.

FIGS. 10A to 10D are schematic cross sections showing the steps for bonding the photoelectric conversion substrate 101 on which the flexible substrate according to the present invention is mounted with the fiber plate in the manufacturing process of the radiation imaging device according to the sixth embodiment.

FIGS. 11A to 11D are schematic cross sections showing the steps for bonding the photoelectric conversion substrate 101, on which the flexible substrate according to the present invention is mounted, with the fiber plate in the manufacturing process of the radiation imaging device according to the sixth embodiment.

Each manufacturing step will be described in detail. The plural photoelectric conversion substrates 101 comprising the flexible substrate 4 are placed on a stage while positioning them using an alignment head movable along the X, Y and Z directions and θ direction (rotation) and an alignment camera. Each photoelectric conversion substrate 101 is fixed on the stage by sucking with a vacuum apparatus through holes formed on the stage (FIG. 9A).

Each imaging element 100 is inspected for its required operation while mounting the photoelectric conversion substrate on the stage. Whether each imaging element is broken or not by electrostatic charge is inspected in this test using an inspection jig (FIG. 9B).

When any defective imaging element 100 is found in this inspection, the vacuum equipment under the corresponding photoelectric conversion element 101 is turned off to replace the defective element using the alignment head (FIG. 9C).

Subsequently, an adhesive such as a UV curing type or silicone resin is coated on the photoelectric conversion element 101 (FIG. 9D).

Then, the flexible substrate 4 is inserted into a slender hole provided on the base substrate 10 and, after allowing the photoelectric conversion element 101 to come to close contact with the base substrate 10, they are bonded by irradiating a UV light and/or by compressing (FIG. 9E)

The size of the fiber plate 2 may be the same as the size of the photoelectric conversion element 101 for positioning them. A glass or permalloy (an iron-nickel alloy) is used for the base substrate 10 considering the difference of the thermal expansion coefficient between the base substrate and the photoelectric conversion element 101.

Then, after bonding the photoelectric conversion element 101 with the base substrate 10, the vacuum apparatus is turned off to remove the photoelectric conversion element 101 and base substrate 10 from the jig such as the stage (FIG. 9F).

Figure 10A:
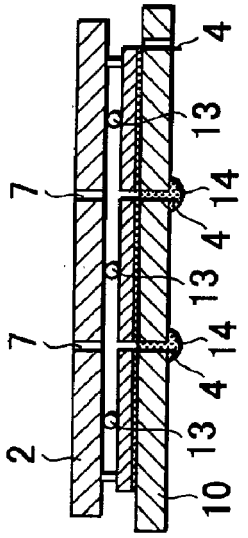
FIGS. 10A to 10D are drawings showing consecutive steps for bonding the substrate on which the flexible substrate according to the present invention is mounted with the fiber plate in the method for manufacturing the radiation imaging device in the sixth embodiment.

The bonding step between the photoelectric conversion substrate and fiber plate will be described hereinafter with reference to FIGS. 10A to 10D. A spacer 13 is placed on each photoelectric conversion substrate 101 bonded to the base substrate 10 so that a gap is secured between the photoelectric conversion substrate 101 and fiber plate 2 (FIG. 10A)

Figure 10B:
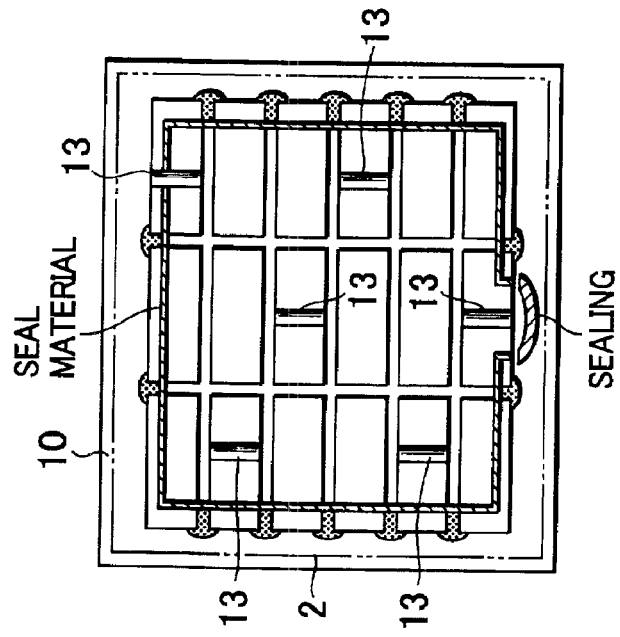

The spacer 13 may be spherical or columnar shape. Then, a seal material and a joint adhesive are coated on the substrate 1 (FIG. 10B).

Figure 10C:
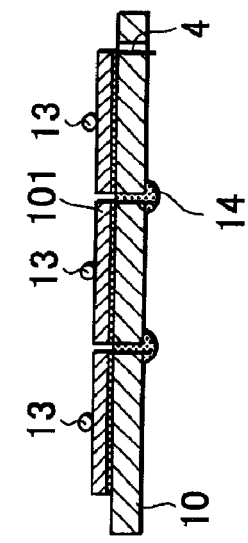

The joint adhesive is used for filling the gap between the photoelectric conversion substrates 101. A part of the seal layer is open as shown in FIG. 10B, and a transparent adhesive 6 is injected through the opening as will be described hereinafter. The joint adhesive is injected to fill the gap between the photoelectric conversion substrates 101 so that the gap does not create a vacuum leak. Then, the fiber plate 2 is bonded onto the spacer 13 (FIG. 10C).

Figure 10D:
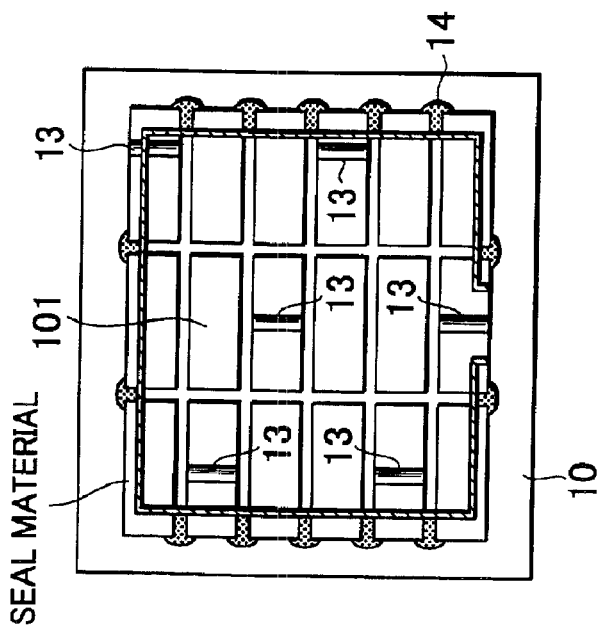

It is preferable that the adhesive 7 for bonding the fiber plates 2 with each other is applied in the gap between the photoelectric conversion substrates 101 or immediately above the space between the pixels. The adhesive is cured after making the space between the photoelectric conversion substrate 101 and fiber plate uniform by compression and heat. Subsequently, after evacuating the gap between the fiber plate and photoelectric conversion substrate 101 in a vacuum chamber, an opening is attached to a port filled with the transparent adhesive 6 followed by returning the vacuum to an atmospheric pressure to fill the transparent adhesive 6 into the gap. The opening is sealed thereafter (FIG. 10D).

A seal resin 15 is coated between the fiber plate 2 and base substrate 10 to allow the photoelectric conversion substrate 101 to be isolated from the external environment.

The X-ray imaging device is manufactured by bonding, for example, the fluorescent layer 3 on the sheet onto the fiber plate 2.

While the fluorescent layer 3 may be provided by depositing a fluorescent material on the fiber plate, or by mixing a fluorescent powder with a binding material followed by coating on the fiber plate, the fluorescent layer 3 is formed on the fiber plate in advance of the step described with reference to FIG. 10C in this embodiment.

When the X-ray imaging device is manufactured from a plurality of X-ray imaging units, the photoelectric conversion substrate 101, base substrate 10 and fiber plate may be laminated with bonding by the steps shown in FIGS. 11A to 11D.

In this method, the fiber plate 2 is ground to meet the area of the photoelectric conversion substrate 101, while grinding both impinging and projection faces of the fiber plate for planarization. Spherical or columnar spacers 13 are disposed on the photoelectric conversion substrate 101 bonded to the base substrate 10 so that a space is provided between the photoelectric conversion substrate 101 and fiber plate 2 (FIG. 11A).

Subsequently, the seal layer 14 is coated on the photoelectric conversion substrate 101 (FIG. 11B).

A part of the seal layer is open as shown in FIG. 11B, an the transparent adhesive 6 is injected through the opening by a vacuum injection method as will be described hereinafter. The joint adhesive is filled in the gap between the photoelectric conversion substrates 101 so that the gap does not cause any leak of vacuum. After positioning the fiber plate 2 on the spacer 13, the fiber plate 2 is bonded to the photoelectric conversion substrate 101 by compression and heating (FIG. 11C).

After evacuating the gap between the fiber plate 2 and photoelectric conversion substrate 101 in the vacuum chamber, an opening is attached to the port filled with the transparent adhesive 6 to return vacuum to an atmospheric pressure, thereby filling the gap with the transparent adhesive 6. The opening is sealed thereafter (FIG. 11D).

The fluorescent layer 3 at the side of the light impinging face of the fiber plate 2 is formed by vacuum deposition, coating or printing. This step is applied either after grinding the fiber plate 2 or after bonding the fiber plate to the photoelectric conversion substrate 101.

Seventh Embodiment

Figure 12:
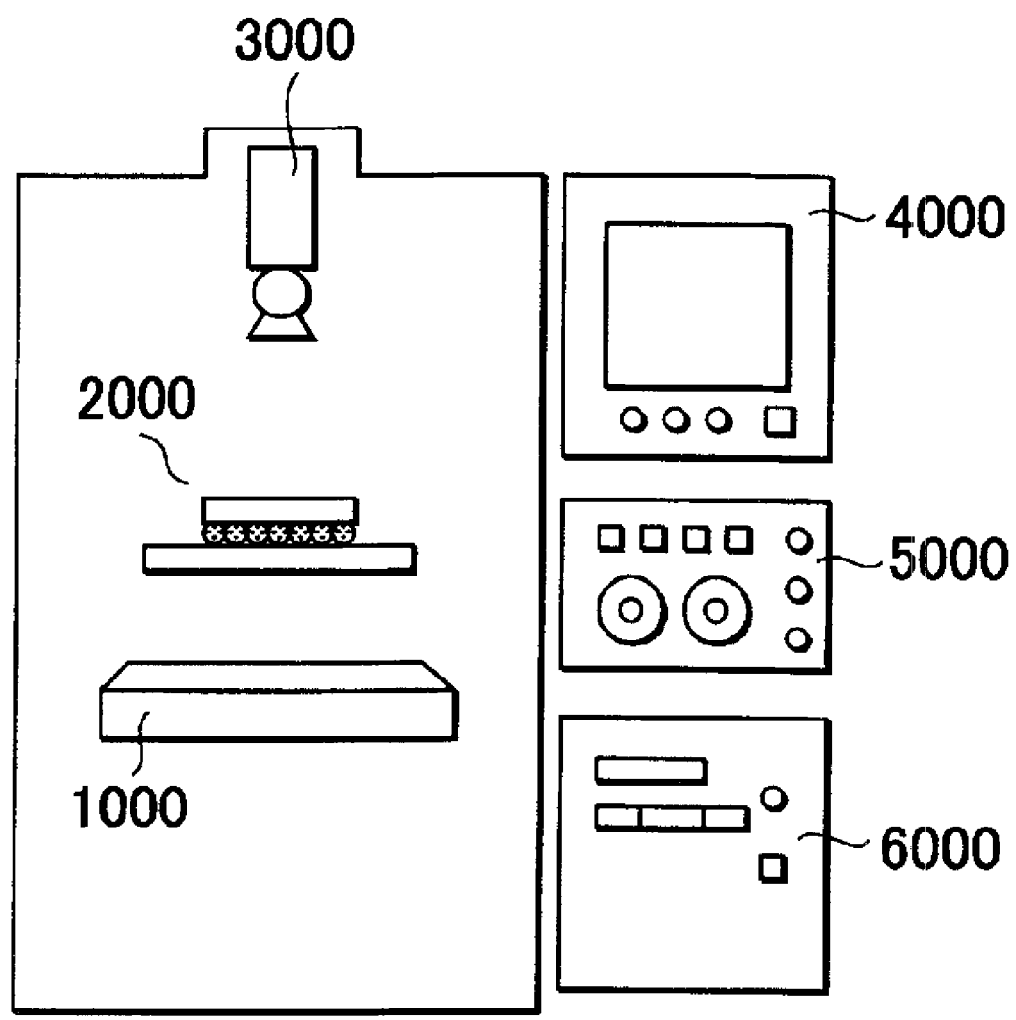
FIG. 12 is a schematic drawing showing the construction of a X-ray diagnosis system comprising the X-ray imaging device according to the present invention.

FIG. 12 is a schematic drawing showing the construction of a non-destructive inspection comprising the radiation imaging device described in the sixth embodiment. In FIG. 12, the reference numeral 1000 denotes the X-ray imaging device described in the first embodiment, the reference numeral 2000 denotes an imaging object as an object of the non-destructive inspection to be assembled in electric appliances, the reference numeral 3000 denotes a micro-focus X-ray generator for irradiating a X-ray to the imaging object 2000, the reference numeral 6000 denotes an image processor for processing signals exported from the X-ray imaging device 1000, the reference numeral 4000 denotes a monitor for displaying the image processed in the image processor 6000, and the reference numeral 5000 denotes a controller for operating the image processor 6000 and monitor 4000.

In the non-destructive inspection system shown in FIG. 12, the X-ray generated from the micro-focus X-ray generator 3000 is irradiated to the imaging object 2000 that is subjected to non-destructive inspection. Then, a line of information of defects, if any, in the imaging object 2000 is exported to the image processor 6000 through the X-ray imaging device 1000. The image processor 6000 displays the exported signal as an image on the monitor 4000 after processing the image signal among the peripheral pigments on the imaging element 1 or applying a dark correction.

The image displayed on the monitor 4000 can be magnified or contracted, or adjusted for light and shade, by instruction from the controller 5000. Consequently, defects within the imaging object 2000, if any, may be inspected through the image displayed on the monitor 4000. When no defects are found in the imaging object 2000, it is considered to be good and is integrated into electric appliances. When some defects are found in the imaging object, on the other hand, it is considered to be bad and is eliminated from the manufacturing process.

Eighth Embodiment

Figure 13:
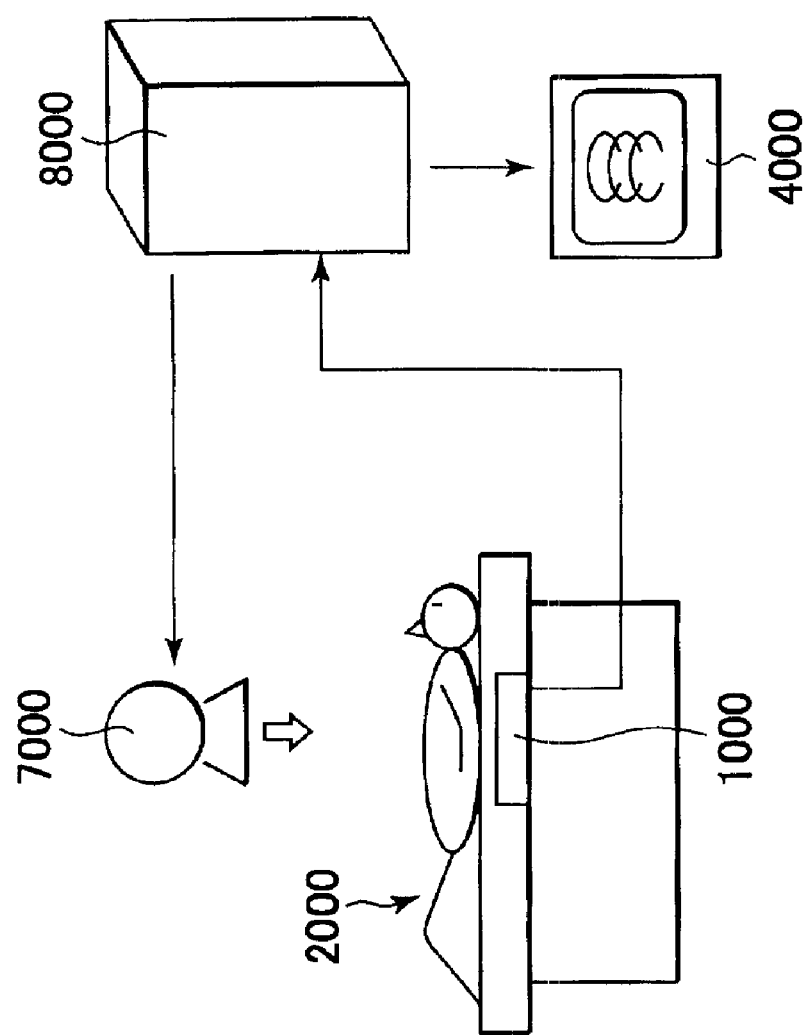
FIG. 13 is a schematic drawing showing the construction of a X-ray diagnosis system comprising the X-ray imaging device according to the present invention.
Figure 14:
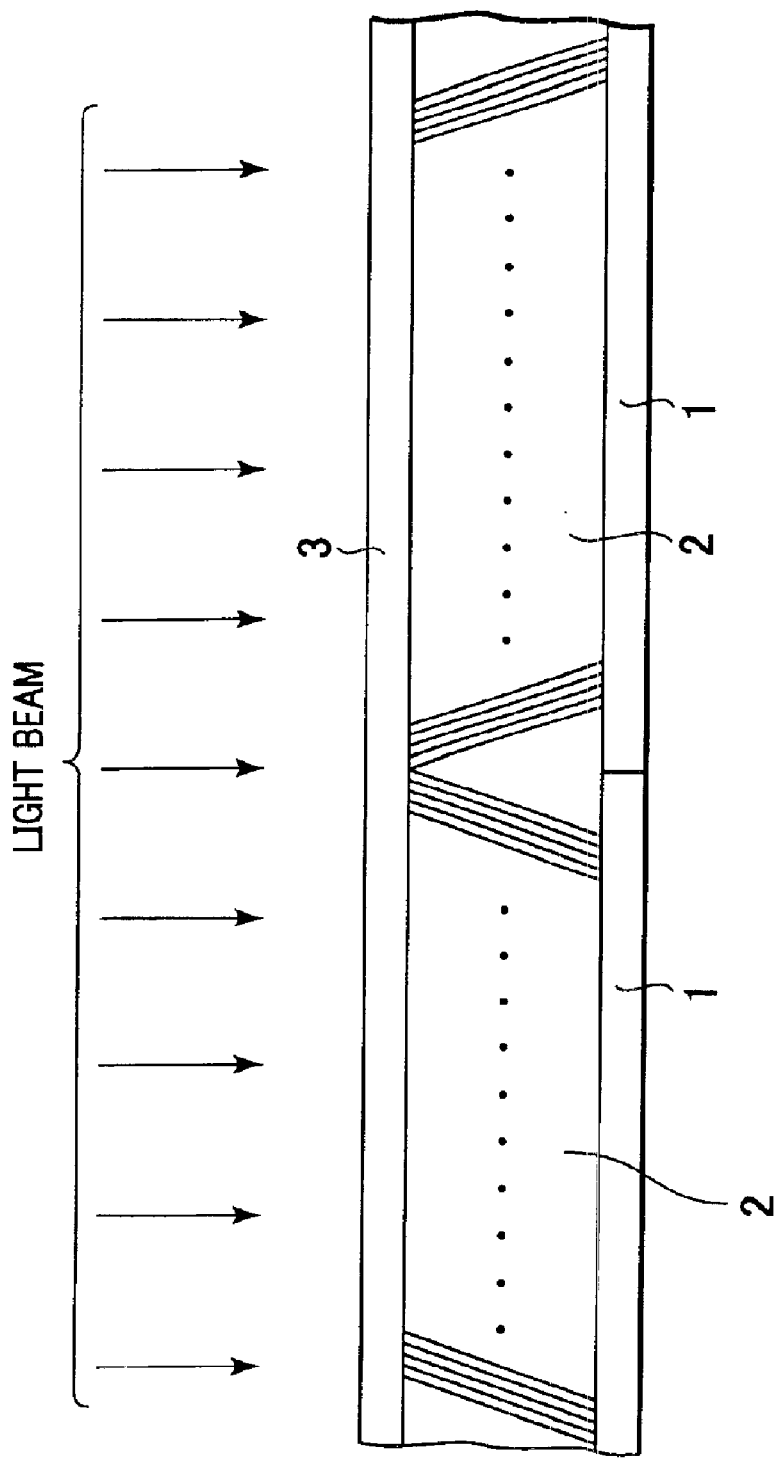
FIG. 14 is a schematic cross section of a conventional X-ray imaging device.
Figure 15:
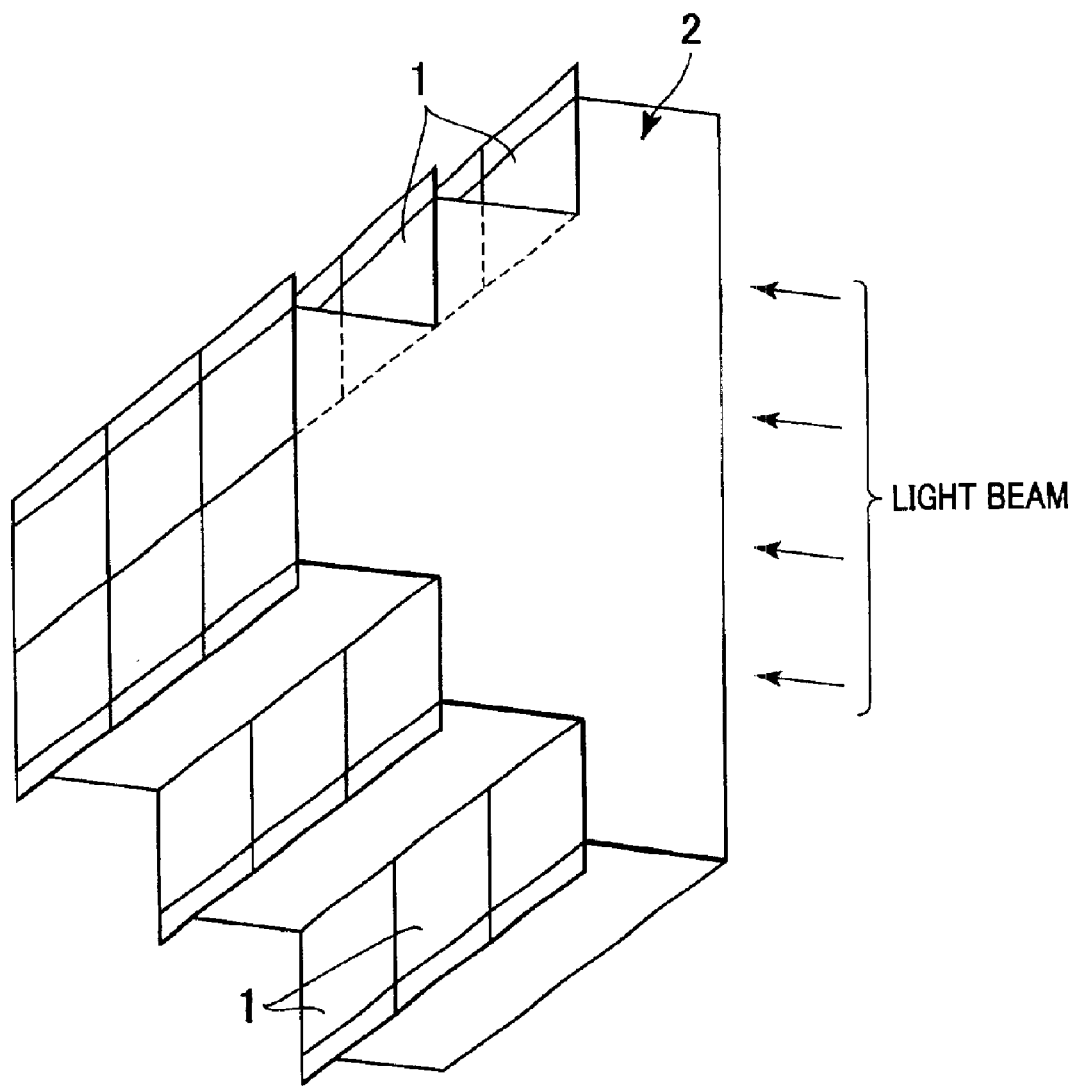
FIG. 15 is a schematic perspective view in a conventional art with a different construction of the X-ray imaging device.

FIG. 13 is a schematic drawing showing the construction of a X-ray diagnosis system comprising the X-ray imaging device according to the present invention. FIG. 13 shows a bed comprising the X-ray imaging device 1000, a X-ray generator 7000 for irradiating an imaging object 2000 with the X-ray, an image processor 8000 for processing image signals exported from the X-ray imaging device 1000 and for controlling the timing of X-ray irradiation from the X-ray generator 7000, and a monitor 4000 for displaying the image signal processed by the image processor 8000. The same reference numerals are attached to the same elements in FIG. 13 as those shown in FIG. 12.

In the X-ray diagnosis system shown in FIG. 13, the X-ray generator 7000 generates an X-ray based on the instruction from the image processor 8000, and irradiates the X-ray to the imaging object 2000 on the bed. Then, a line of X-ray image information of the imaging object 2000 is exported to the image processor 8000 through the X-ray imaging device 1000. The image processor 8000 stores the exported signal in a memory (not shown) or displays the image on the monitor 4000, after processing the image signal among the peripheral pigments on the imaging element 1 or applying a dark correction.

The image displayed on the monitor 4000 can be magnified or contracted, or adjusted for light and shade, by instruction from the image processor 8000. The doctor can examine the imaging object 2000 with reference to the image displayed on the monitor 4000.

The X-ray image information of the imaging object 2000 after the examination by the doctor may be recorded on a recording medium disk by providing a recording device in the system.

While use of the X-ray has been described in each embodiment of the present invention, other radiations such as α-, β- and γ-ray may be used as well. The light includes any electromagnetic wave such as a visible light detectable by the pixel. The present invention also may be applied for a device for converting the electromagnetic wave including radiation into an electrical signal.

While a photoelectric conversion device has been described in each embodiment, the present invention may be also applied for a large screen display device in which a plurality of substrates of the display elements are bonded on a plane.

While the present invention has been described with reference to what are presently described to be the preferred embodiment, it is to be understood that the invention is not limited to the disclosed embodiments. On the contrary, the invention is intended to cover various modifications and equivalent arrangements included within the spirit and scope of the appended claims. The scoped of the following claims is to be accorded the broadest interpretation so as to encompass all such modifications and equivalent structures and functions.

What is claimed is:

1. A semiconductor device comprising:
   a substrate comprising a semiconductor element, an external connection face on which an external connection terminal is formed and a side face; and
   a flexible substrate comprising an inner lead and a base film formed on the inner lead, with one end of the inner lead being connected to the external connection terminal, wherein an area of the base film is thinner than the external connection terminal, said area of the base film being disposed above the edge of the external connection face closest to the side face.

2. An imaging device comprising a semiconductor device according to claim 1, wherein the substrate comprising the semiconductor element, the external connection face and the side face is a photoelectric conversion substrate.

3. An imaging device according to claim 2, comprising a plurality of photoelectric conversion substrates.

4. The imaging device according to claim 3, wherein the flexible substrate is disposed among a plurality of photoelectric conversion substrates.

5. A radiation imaging device comprising a scintillator formed on the imaging device according to claim 2.

6. A radiation imaging system comprising:

the imaging device according to claim 2, a signal processing means for processing a signal from the radiation imaging device;

a recording means for recording a signal from the signal processing means;

a display means for displaying the signal from the signal processing means; and a transfer means for transmitting the signal from the signal processing means.

7. A semiconductor device comprising:

a photoelectric conversion substrate having an external connection face on which an external connection terminal is formed and a side face; and a flexible substrate one end of which is connected to the external connection terminal, wherein the flexible substrate is disposed along the external connection face and the side face, and a corner between the external connection face and the side face is chamfered.

8. A semiconductor device according to claim 7, wherein the external connection terminal is a bump.

* * * * *